United States Patent [19]

Foster et al.

[11] 4,059,617

[45] Nov. 22, 1977

[54] SYNTHESIS OF DIMETHYLAMINOETHYL METHYLMETHACRYLATE

[75] Inventors: Terence Foster, Clayton; Thomas Stephen Dawson, Guiseley, both of England

[73] Assignee: American Cyanamid Company, Stamford, Conn.

[21] Appl. No.: 681,679

[22] Filed: Apr. 29, 1976

[51] Int. Cl.$^2$ .............................................. C07C 69/54
[52] U.S. Cl. .................................................... 560/222
[58] Field of Search .................................... 260/486 R

[56] References Cited

FOREIGN PATENT DOCUMENTS 976,304  11/1964  United Kingdom ............ 260/486 R

*Primary Examiner*—Paul J. Killos
*Attorney, Agent, or Firm*—Gordon L. Hart

[57] ABSTRACT

Yield of dimethylaminoethyl methacrylate from the reaction of methacrylic acid with dimethylaminoethanol is increased by carrying out the reaction under reflux conditions in presence of catalyst selected from sodium phenoxide and sodium 4-methoxyphenoxide and with incremental addition of the dimethylaminoethanol as the reaction proceeds. Yields as high as 89 percent are reported.

5 Claims, No Drawings

SYNTHESIS OF DIMETHYLAMINOETHYL METHYLMETHACRYLATE

The invention relates to the synthesis of dimethylaminoethyl methacrylate by alcoholysis of methylmethacrylate.

British patent specification No. 976,304 described the method of preparation of an ester of methacrylic acid by the transesterification reaction of a primary or secondary alcohol with an ester of methacrylic acid which is lower boiling than the desired ester product, in presence of an alkali phenate catalyst and preferably also in presence of a polymerization inhibitor. The process was described as being of particular utility when the alcohol reactant was an alcohol other than dimethylaminoethanol. The improvements were said to be less marked when that particular amino compound was used as the alcohol reactant.

The present invention deals in particular with the alcoholysis of methylmethacrylate with dimethylaminoethanol and provides an improved process that gives a product in high yields. It is reasoned that the problem with the use of dimethylaminoethanol for the reactions described by the British patent was that dimethylaminoethanol is subject to decomposition under the reaction conditions described there. As the reaction would proceed, the breakdown of the reactant alcohol would compete with the alcoholysis reaction, resulting in unimpressive yields.

By the selection of optimum catalysts that provide maximum activity, the reaction time is minimized so that the decomposition of reactant in the reaction mixture is also minimized. Furthermore the alcohol reactant is added gradually over the course of the reaction to minimize the exposure of this reactant to the reaction conditions under which the reactant is unstable. Notwithstanding an expected adverse decrease in reaction rate due to the lower alcohol reactant concentration in the reaction mixture, it is found that the gradual addition technique will result in a significantly higher yield than would be obtained if the entire alcohol reactant were charged to the reactor at the start.

The preferred phenate catalysts for use in the invention are the alkali metal phenoxides from phenol or 4-methoxy phenol. The sodium phenoxides are the preferred catalysts and are selected for the examples below. We prefer to employ the same in situ preparation of the catalyst which was described in the British patent and so we add the selected phenol or 4-methoxy phenol to the reaction mixture at the start and add sodium methoxide gradually as the reaction proceeds, producing the phenoxide catalyst gradually during the course of the reaction. Since the reaction rate is important for maximum yield, we prefer to employ a reflux apparatur of high efficiency in order to most effectively remove the methanol reaction product as it is formed and thereby avoid retarding the reaction rate.

The reaction is carried out with enough excess methylmethacrylic present in the reactor to provide the necessary reactant and enough more to make the azeotrope of methylmethacrylate with the product methanol which distills over and is removed as the reaction proceeds. We prefer to start with about 1.75 moles methylmethacrylate per mole of aminoalcohol reactant to be added. This ratio may be varied from about 2 to 1 to about 1.25 to 1 but the yield may fall some due to higher pot temperature as the ratio is reduced below 1.75; any unnecessary excess beyond two moles of methylmethacrylate would only burden the product purification. The phenol in the reaction mixture is kept at excess over the sodium methoxide at all times and we prefer to start with from about 5 to about 20 percent molar excess of the phenol over the amount of methoxide to be added. For maximum yield we employ the catalyst in an amount about 2.5 to 3.5 mole percent based on the total dimethylaminoethanol to be added. At lower catalyst levels, the reaction time will increase, resulting in reduced yield.

The rate of addition of the aminoalcohol reactant is adjusted to maintain the aminoalcohol at concentration needed for a vigorous steady reaction as the alcohol reactant is consumed and as methanol by-product is removed and yet to avoid build-up of excess aminoalcohol concentration in the reactor. In other words, the rate of continuous addition is about the same as the rate of consumption at steady state. The alkali methoxide addition ratio is adjusted to provide a steady addition of catalyst throughout the course of the reaction. When using efficient reflux equipment the reaction can be completed in about 40 to 60 minutes.

The reaction product remains in the reactor and can be purified as necessary by any suitable method. For the preparation of a product that is suitable for use as a monomer reactant in free radical polymerization we prefer to distill the product from a heavy oil to separate high boiling impurities.

When a polymerization inhibitor is used in the reaction mixture we prefer to use phenothiazene as inhibitor but other suitable inhibitors could be used. Hydroxydiphenylamine is not preferred as an inhibitor as it would reduce yield. Also hydroquinone is not preferred as it causes the sublimation of excess phenol as it is being removed by distillation during the purification.

The invention is described in more detail by reference to certain specific examples embodying this invention, as set out below.

EXAMPLE 1

A solution of 2.8 gm sodium methoxide (0.05 mole) in 11 gm dry methanol is added to 150 gm dimethylaminoethanol (1.7 moles) and the solution is set aside to be added continuously to the reactor during the reaction. In a 500 ml reactor, equipped with an efficient, packed column with a reflux ratio head for distillation, a mixture is prepared of 338 gm of methylmethacrylate (3.4 moles), 8 gm of 4-methoxy phenol (0.065 mole) and 2.5 gm of phenothiazine (7000 ppm on methylmethacrylate). The mixture is heated in the reactor to about 95° C. and dropwise addition of the dimethylaminoethanol, sodium methoxide mixture is begun and continued at a rate to maintain vigorous reaction as the alcohol reactant is consumed. Heat is supplied as needed to distill off the methanol-methylmethacrylate azeotrope as methanol is formed, while maintaining head temperature in the column at 64.5° C. After all of the alcohol reactant has been added and when the head temperature rises to 65.5° C. the reaction is stopped. The reaction time is 70 minutes and the methanol recovered indicates 99 percent complete reaction. The reactor contents is filtered, mixed with one-third its volume of a high boiling hydrocarbon oil and distilled under vacuum. The yield of distilled dimethylaminoethyl methacrylate is 220 gm, 89 percent of theoretical, b.p. 68° C. at 10 mm Hg.

EXAMPLE 2

In a 500 ml flask fitted with a stirrer thermometer and a long packed column connected to a reflux ratio head, are placed methylmethacrylate (339 gm, 3.4 moles), phenol (5.0 gm, 0.053 moles) and phenothiazine (2.5 gm, 7000 ppm on methylmethacrylate). The mixture is then heated to about 90° C., and a solution of sodium methoxide (14 gm of 20 percent solution in dry methanol — i.e. 2.8 gm, 0.05 mole) in dimethylaminoethanol (150 gm, 1.7 moles) is added dropwise continuously throughout the course of the reaction. Heating is maintained with reflux and 85.5 gm of methylmethacrylatemethanol is collected at a head temperature of 64.5° C.; the reaction is terminated when the head temperature rises to 65.5° C. The total reaction time is 1 hr. and methanol collected indicates that the reaction is better than 98 percent complete.

The mixture is filtered to remove caustic floc and is mixed with one-third its volume of a high-boiling hydrocarbon oil. This mixture is distilled under reduced pressure using a short column. The distillate contains 147 gm methylmethacrylate and 9.5 gm dimethyaminoethanol and the residue is further distilled under vacuum to yield 216 gm, 88 percent theoretical, of dimethylaminoethyl methacrylate, b.pt. 68° C. at 10 mm Hg.

By way of comparison with the above examples, when the entire charge of the dimethylaminoethanol is added at the beginning of the reaction, the yield is found to be considerably reduced, as had been predicted in the British 976,304 patent. Even when the reaction is started with one-third of the aminoalkanol reactant and two other increments of one-third each are added periodically as the reaction proceeds, a somewhat reduced yield, viz. 83.5 percent as compared with 88 percent, is obtained. As addition of smaller and smaller regular increments approaches continuous addition, the yield will approach the maximum. The use of phenoxide catalysts other than those specified in the examples above will result in significantly reduced yields.

The reaction is carried out without water but we have found that suitably high yields are obtained by the process of the invention without special drying of any of the reactant or catalyst ingredients. The purification of the product by distillation from a high-boiling inert liquid such as heavy hydrocarbon oil is preferred to effect the separation of the product from certain high-boiling impurities, the identification of which has not been determined but which are found to interfere with free radical polymerization processes in which the ester product is a useful reactant.

We claim:

1. In the synthesis of dimethylaminoethyl methacrylate by reaction of dimethylaminoethanol with methylmethacrylate in presence of a phenoxide catalyst under reflux conditions with removal of methanol-methylmethacrylate azeotrope by distillation as methanol is produced, the improvement wherein the sodium phenoxide catalyst is selected from sodium phenoxide and sodium 4-methoxyphenoxide and wherein the dimethylaminoethanol reactant is added continuously or regularly in small increments to the reaction mixture from the start and throughout the course of the reaction at a rate about the same as the rate at which the alcohol reactant is consumed.

2. An improved synthesis defined by claim 1 wherein the sodium phenoxide catalyst is prepared in situ by reaction of sodium methoxide, which is added in increments throughout the course of the reaction, with phenol or 4-methoxyphenol in the reaction mixture.

3. An improved synthesis defined by claim 2 wherein the catalyst is sodium phenoxide.

4. An improved synthesis defined by claim 2 wherein the catalyst is sodium 4-methoxyphenoxide.

5. An improved process defined by claim 2 wherein the product dimethylaminoethyl methacrylate is separated by mixing the reaction residue in high-boiling inert liquid and distilling the product from such mixtures under reduced pressure.

* * * * *